US009618476B2

(12) United States Patent
Goldsmith

(10) Patent No.: US 9,618,476 B2
(45) Date of Patent: Apr. 11, 2017

(54) SYSTEM AND METHOD FOR ELECTRONIC BIOLOGICAL SAMPLE ANALYSIS

(71) Applicant: Nanomedical Diagnostics, Inc., San Diego, CA (US)

(72) Inventor: Brett Goldsmith, San Diego, CA (US)

(73) Assignee: NANOMEDICAL DIAGNOSTICS, INC., San Diego, CA (US)

( * ) Notice: Subject to any disclaimer, the term of this patent is extended or adjusted under 35 U.S.C. 154(b) by 0 days.

(21) Appl. No.: 14/263,954

(22) Filed: Apr. 28, 2014

(65) Prior Publication Data

US 2015/0309018 A1    Oct. 29, 2015

(51) Int. Cl.
  *G01N 27/414*    (2006.01)
  *G01N 33/543*    (2006.01)
  *B01L 3/00*    (2006.01)

(52) U.S. Cl.
  CPC .... *G01N 27/4145* (2013.01); *B01L 3/502715* (2013.01); *G01N 33/54373* (2013.01); *B01L 3/502707* (2013.01); *B01L 2200/027* (2013.01); *B01L 2300/0636* (2013.01); *B01L 2300/0645* (2013.01)

(58) Field of Classification Search
  CPC .......... G01N 27/4145; G01N 33/54373; B01L 3/502707; B01L 3/502715
  See application file for complete search history.

(56) References Cited

U.S. PATENT DOCUMENTS

| | | | |
|---|---|---|---|
| 8,445,945 | B2 | 5/2013 | Rothberg et al. |
| 9,339,790 | B2 * | 5/2016 | Vittadello |
| 2004/0238379 | A1 | 12/2004 | Lindsay et al. |
| 2010/0255984 | A1 * | 10/2010 | Sutter ............. B82Y 30/00 502/185 |
| 2010/0279426 | A1 * | 11/2010 | Tour .............. B82Y 10/00 436/149 |
| 2010/0327847 | A1 | 12/2010 | Leiber et al. |
| 2011/0217763 | A1 | 9/2011 | Rasooly et al. |
| 2012/0214172 | A1 | 8/2012 | Chen et al. |
| 2012/0220053 | A1 * | 8/2012 | Lee ............. H01L 29/4908 436/501 |
| 2013/0270521 | A1 | 10/2013 | Peng et al. |

(Continued)

FOREIGN PATENT DOCUMENTS

| | | |
|---|---|---|
| WO | 2012050646 A2 | 4/2012 |
| WO | WO2012/112746 * | 8/2012 |

OTHER PUBLICATIONS

Nguyen et al. "Graphene Interfaced with Biological Cells: Opportunities and Challenges," The 5 Journal of Physical Chemistry Letters, 2012, vol. 3, pp. 1024-1029.

(Continued)

*Primary Examiner* — Melanie Y Brown
(74) *Attorney, Agent, or Firm* — Sheppard, Mullin, Richter & Hampton LLP

(57) ABSTRACT

A biological sample analysis device includes a casing that encloses a biological sample delivery system hydraulically coupled to a sensor, wherein the sensor includes a plurality of Graphene transistors and each transistor covalently bonds with a biomarker causing the electrical properties of the transistor to measurably change when the biomarker is exposed to corresponding antibodies within an infected biological sample.

8 Claims, 16 Drawing Sheets

(56) References Cited

U.S. PATENT DOCUMENTS

| | | | | |
|---|---|---|---|---|
| 2014/0042390 A1* | 2/2014 | Gruner | ............... | H01M 4/364 257/14 |
| 2014/0162390 A1* | 6/2014 | Afzali-Ardakani | | G01N 33/5438 438/49 |
| 2014/0312879 A1* | 10/2014 | Torsi | ............... | G01N 27/4145 324/76.11 |
| 2015/0038378 A1* | 2/2015 | Cheng | ............... | G01N 33/5438 506/39 |
| 2015/0218094 A1* | 8/2015 | Braunschweig | ....... | B82Y 30/00 548/455 |
| 2015/0276709 A1* | 10/2015 | O'Halloran | ....... | B01L 3/502761 506/6 |
| 2016/0123919 A1* | 5/2016 | Johnson | ........... | G01N 33/54373 506/38 |

OTHER PUBLICATIONS

Mohanty et al. "Graphene-Based Single-Bacterium Resolution Biodevice and DNA Transistor: Interfacing Graphene Derivatives with Nanoscale and Microscale Biocomponents" Nano Lett., Nov. 5, 2008, vol. 8, No. 12, pp. 4469-4476.

Patent Cooperation Treaty, International Search Report for PCT/US2015/026254, Jul. 16, 2015, pp. 1-2.

Patent Cooperation Treaty, International Search Report for PCT/US2016/026730, Jul. 15, 2016, pp. 1-2.

* cited by examiner

SYSTEM AND METHOD FOR ELECTRONIC BIOLOGICAL SAMPLE ANALYSIS

TECHNICAL FIELD

The present disclosure is directed towards electronic biological sample analysis.

BACKGROUND

Diagnostic technologies directed towards detecting viral or bacterial infections, or other ailments, within a biological sample generally do not have the sensitivity to directly detect the presence of infectious agents such as a bacteria, virus, or diseased tissue (e.g. cancer) before an immune response occurs. Thus, most diagnostic technologies detect such infections or ailments through detection of antibodies created by a patient's immune system in response to the particular condition. For example, these antibody detection techniques are currently not capable of detecting many diseases within the first month of infection (e.g. Lyme disease). There are laboratory scale analytical and sample treatment techniques capable of detecting markers at an early stage of infection. However, these laboratory techniques require time, expertise and material that prevent common clinical use. One of these laboratory scale sensors is based on direct detection using carbon nanotube devices. Such sensors have been developed in academic labs worldwide. A related material, Graphene, has seen less academic development, but is widely understood to have similar potential use. However, these specialized nanoelectronics lab technologies have yet to be converted into a practical diagnostic systems or methods.

Generally, biological sample analysis to determine the presence of antibodies may be performed on blood or urine samples. Current blood diagnostic systems rely on technologies including enzyme-linked immunoassay (ELISA), gel electrophoresis and blood culture. These are all proven, mature technologies. All three of these tests require significant time to run, from several hours to several days.

ELISA and gel electrophoresis tests generally measure an immune system response to a disease (e.g. the presence of antibodies), rather than presence of the disease itself. Most diagnostic tests, including ELISA and gel electrophoresis tests, require detection of a reporter molecule or molecular label. In these tests a reporter or amplifier molecule is required to generate a measurable signal.

All of these tests require either significant expertise or very expensive automation equipment to run. This is partly due to the multiple steps and specialized reagents required. For example, ELISA tests are particular complicated. ELISA tests include coating a measurement well or surface with a copy of a chemical marker created by an infectious agent known as an antigen, incubating a biological sample (e.g. blood, serum, urine, or cerebrospinal fluid), and exposing the measurement well to the biological sample to allow the antibody, if present, to bind to the antigen. The binding process is subject to thermodynamic laws of probability and is not perfect such that some antibodies will bind incorrectly or fail to bind where they should. The ELISA test further includes washing the patient sample from the well, adding a solution with a reporting antibody intended to bind to antibodies bound to the well wall, rinsing the well a second time, and adding a reporting dye to the intended to change colors in the presence of reporting dye. These steps are also subject to variances in binding efficiency and accuracy.

Gel electrophoresis tests are also complicated. In many cases, ELISA is generally preferred for cost and difficulty. Not all infectious agents can be detected by using a blood culture, for example infection with Borelia burgdoferi is not generally identified via blood culture. The complexity of these tests makes them extremely operator dependent, creating the possibility for variance in test result accuracy depending on the experience and skill of the operator. Automation could improve accuracy and decrease testing variance, but no such automated solutions are readily available.

Another biological sample analysis technique is based on the polymerase chain reaction (PCR), which clones targeted small fragments of DNA. This is a highly sensitivity technique, but also requires either significant expertise or very expensive automated equipment to run properly, and requires several hours for each test.

All of these currently available tests are costly, highly operator dependent, and lack the sensitivity specificity to accurately and reliably detect many diseases, particularly in the disease's early states (e.g. Lyme disease).

SUMMARY OF EMBODIMENTS

The present disclosure is directed towards an electronic biological sample analysis system and method. In particular, the present disclosure is directed towards direct detection of disease and/or infection using a nanoelectronic circuit by enabling bonding of antibodies directly with an electronic circuit in the testing device, exposing the testing device to a biological sample, and measuring changes in electrical properties of the electronic circuit-antibody system. The changes in electrical properties are analyzed to determine the presence of infection in the sample. This technique can be extraordinarily sensitive, and can be engineered to drastically minimize the effects of improper antibody binding.

As disclosed herein, an example system for electronic biological sample analysis includes an electronic biological sample sensor system wherein the biological sample sensor system includes a sensor chip electronically coupled to an external connector wherein the sensor chip includes one or more transistors, each transistor includes one or more scattering sites, and each scattering site includes one or more covalently bonded biomarkers. In several embodiments, the transistors comprise Graphene. In some examples, the transistors comprise $sp^2$ hybridized Carbon and $sp^3$ hybridized Carbon, wherein at least $sp^3$ hypbridized Carbon molecules covalently bond to biomarker molecules such that the electrical properties of the transistor change when exposed to biological samples from patients with infections or diseases corresponding to the biomarker.

Some embodiments of the disclosure further include a liquid handling system and a casing shaped to form a liquid-tight and internally located sample chamber. The electronic biological sample sensor system and the liquid handling system are encapsulated in the casing. In some embodiments, the liquid delivery system includes a sample chamber and one or more flanges hydraulically coupled to the sample chamber, wherein the sample chamber forms a liquid-tight seal against the sensor chip.

Also as disclosed herein, an example method for electronic biological sample analysis includes introducing a biological sample to an electronic biological sample analysis sensor, applying voltage to the electronic biological sample analysis sensor, measuring current from the biological sample analysis sensor, comparing the measured current with a baseline current, and returning a "test positive" if the change in current exceeds a predetermined threshold. For example, the biological sample may be a urine, blood, serum, or cerebral fluid sample. The steps of introducing a biological sample, applying voltage, and measuring current may be repeated and alternated in a cycle with flushing the biological sample analysis sensor with a sterile solution. Repeating these steps will increase the statistical significance of the results and reduce sampling noise.

BRIEF DESCRIPTION OF DRAWINGS

The present disclosure, in accordance with one or more various embodiments, is described in detail with reference to the following figures. The figures are provided for purposes of illustration only and merely depict typical or example embodiments of the disclosure.

The figures are not intended to be exhaustive or to limit the disclosure to the precise form disclosed. It should be understood that the disclosure can be practiced with modification and alteration, and that the disclosure can be limited only by the claims and the equivalents thereof.

DETAILED DESCRIPTION

Embodiments of the present disclosure are directed toward systems and methods for performing biological sample analysis. In some examples, a system for biological sample analysis includes an outer casing, a biological sample delivery system, and an electronic biological sample sensor system. The biological sample delivery system may be configured to deliver a liquid biological sample externally located from the biological sample analysis system to the biological sample sensor system via one or more tubes coupled to a sample chamber, wherein at least one side of the sensor chamber is exposed to a sensor chip in the electronic biological sample sensor system. In several examples, the electronic biological sample sensor system includes the sensor chip and an electronic connector, electrically coupled to the sensor chip, wherein the electronic connector is configured to deliver source-drain voltage and source-gate bias to transistors in the sensor chip, as well as to monitor current flow from the transistors that corresponds to the presence of particular antibodies (e.g. antibodies for Lyme disease) within the biological sample.

Figure 1:
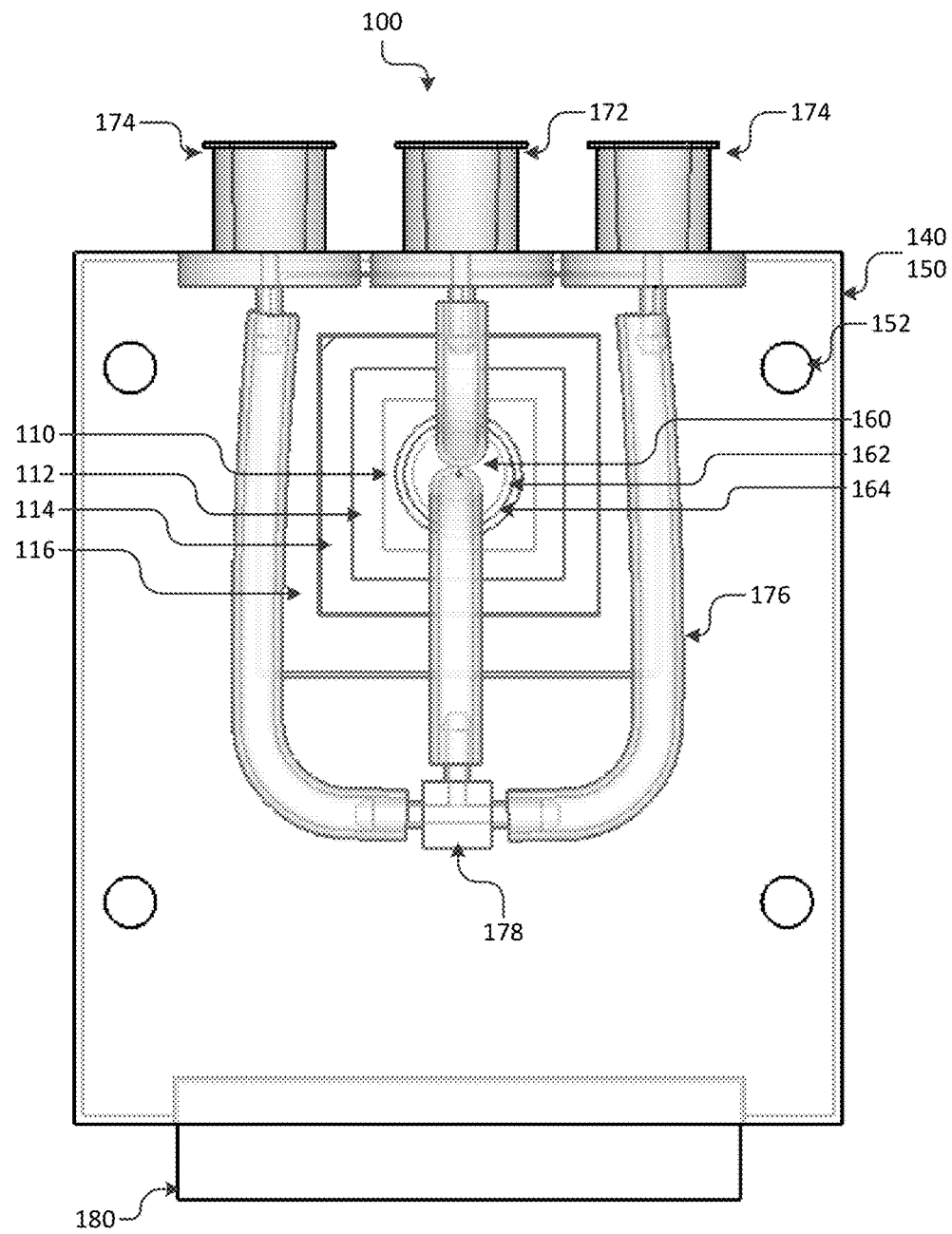
FIG. 1 illustrates a top view of a biological sample analysis device consistent with embodiments disclosed herein.

FIG. 1 illustrates a top view of an example biological sample analysis device. An example biological sample analysis device 100 an outer casing comprising a first cartridge half 140 and a second cartridge half 150 configured to fit together to form a sealed enclosure. First cartridge half 140 and second cartridge half 150 may be aligned and secured together with screws, bolts, tabs, dowels, or other fasteners inserted through mounting holes 152. For example, four mounting holes 152 in first cartridge half 140 may be aligned with four mounting holes 152 in second cartridge half 150 to properly align the two cartridge halves, and then fasteners may be inserted through the holes to secure the halves together.

The external casing of biological sample analysis device 100, in general, is configured to encapsulate an electronic biological sample sensor system enclosed therein. In some examples, the external casing of biological sample analysis device 100 may comprise an outer casing that is a single molded component wherein the molded component comprises plastic, foam, rubber, acrylic, or any other moldable material that is sufficiently water tight. In other examples, the first cartridge half 140 may be hingedly coupled to second cartridge half 150. First cartridge half 140 may also snap fit, press fit, or lock in place when oriented in a closed position with respect to second cartridge half 150 such that the two cartridge halves together form a single cartridge. In some examples, first cartridge half 140 and second cartridge half 150 are aligned using alignment pins or dowels protruding from either the first or the second of the cartridge half, and inserting said alignment pins into alignment holes 152 on the other cartridge half. In one such example, the two cartridge halves may be snap fit, form fit, or press fit together. Other methods of manufacturing a watertight external cartridge casing that are possible as would be known in the art, so long as the external cartridge casing, at least, encloses sample chamber 160 and sensor chip 110.

Still referring to FIG. 1, second cartridge half 150 may further comprise a sensor chip 110, a chip carrier 112, a carrier socket 114, a circuit board 116, and an external connector 180. For example, circuit board 116 may be mounted or form fit inside of second half casing 150 and may be electronically coupled to external connector 180. Circuit board 116 may also support and electronically couple to carrier socket 114, which in turn may support and electronically couple to chip carrier 112. Chip carrier 112 may be configured to physically support and electronically couple to sensor chip 110.

In some examples, sensor chip 110 is a Graphene chip with one or more Graphene transistors, as disclosed herein. The Graphene chip may comprise a plurality of electronic scattering sites located on a top surface of the Graphene chip, wherein each scattering site includes covalently bonded biomarkers that correlate to particular antibodies generated by the human body in reaction to particular infections or diseases (e.g. biomarkers selected for their propensity to bond to antibodies generated by the human body in response to Lyme disease). Further, each scattering site is located on a particular Graphene transistor. The scattering sites are further configured to change the electrical properties of the particular Graphene transistor when the scattering site is exposed to the antibody or antibodies that correlate to the particular bonded biomarker. Accordingly, by applying voltage across the source and drain of each transistor, and properly biasing the source and gate voltage, each Graphene transistor is configured to switch on and/or increase current flow when exposed to a liquid sample containing the antibody or antibodies that correlate to the particular biomarkers bonded to the Graphene transistor's scattering site.

Sensor chip 110 may electrically couple to chip carrier 112. For example, sensor chip 110 may be wire bonded to chip carrier 112. In several embodiments, chip carrier 112 also supports and holds in place sensor chip 110.

Chip carrier 112 may electrically couple to carrier socket 114. In several embodiments, carrier socket 114 supports and holds in place chip carrier 112. Chip carrier 112 may be further configured to snap fit, form fit, or press fit into carrier socket 114 such that electrical leads extending from chip carrier 112 both mechanically and electrically couple to carrier socket 114, but may be mechanically released from carrier socket 114.

Carrier socket 114 may electrically couple to circuit board 116. In several embodiments, circuit board 116 supports and holds in place carrier socket 114. Circuit board 116 may then electrically couple to electrical connector 180. Other electrical and mechanical orientations of sensor chip 110 with respect to circuit board 116 are possible. For example, sensor chip 110 may directly bond to circuit board 116 through a wire bonding, soldering, flip chip solder ball, or other type of electro-mechanical bond as known in the art. In some embodiments, a wire harness or other electric coupling mechanism may facilitate electric coupling of sensor chip 110 with electrical connector 180 such that circuit board 116 is not required.

Still referring to FIG. 1, a biological sample delivery system may be configured to expose sensor chip 110 to a biological sample. The biological sample delivery system may comprise one or more tubes 176, one or more flanges 172 and 174, and sample chamber 160. Flanges 174 and 172 may hydraulically couple to sample chamber 160 through the one or more tubes 176 such that, if a biological sample is introduced through either flange 172 or 174, the biological sample will flow through the tubes 176, into sample chamber 160, and then, if continued pressure is maintained through one of the flanges 172 or 174, the biological sample may be forced out of sample chamber 160 and out of the other flange or flanges 174 or 172. For example, if flanges 174 input flanges, the flange 172 may act as an exit flange. One of flanges 174 may be used to flush the entire biological sample delivery system with a cleaning solution. Tubes 176 may be hydraulically coupled together with junction 176.

In several examples, sensor chip 110 forms a liquid-tight seal with sample chamber 160. For example, an O-ring 162 may fit within O-ring groove 164 on the outer rim of sample chamber 160, such that when sensor chip 110 is pressed up against sample chamber 160 (e.g. when casing halves 140 and 150 are closed together), O-ring 162 is compressed inside of O-ring groove 164 and against both sample chamber 160 and sensor chip 110, creating a liquid-tight seal.

Figure 2:
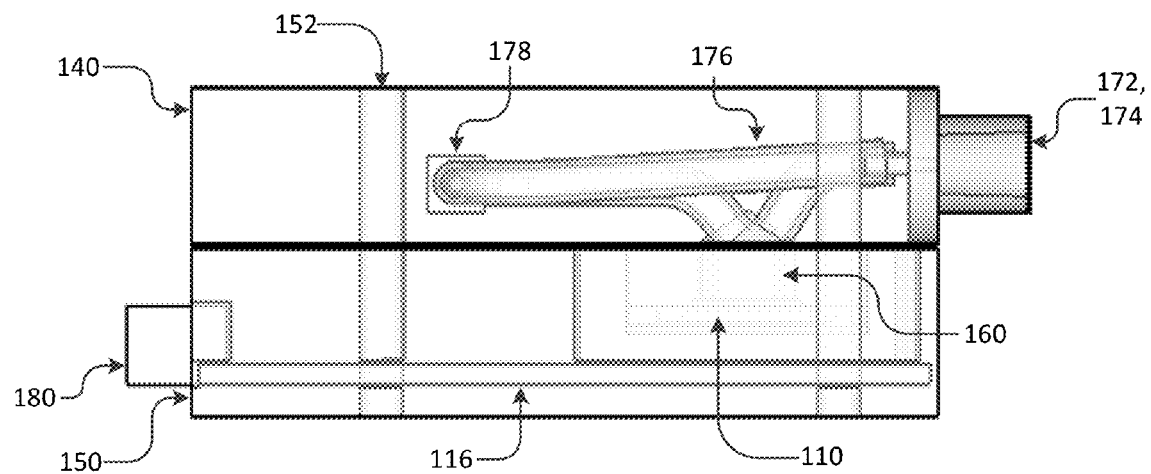
FIG. 2 illustrates a side view of a biological sample analysis device consistent with embodiments disclosed herein.

FIG. 2 illustrates a side view of biological sample analysis device 100. In the non-limiting embodiment illustrated by FIG. 2, casing half 140 is a top half of the casing system and casing half 150 is the bottom half of the casing system. Sample chamber 160 protrudes downward from upper casing half 140 and into bottom casing half 150 when the two halves are configured in the closed position illustrated in FIG. 2. Further, sample chamber 160 is sealed on a bottom side by sensor chip 110 such that, when a biological sample is introduced through flanges 172 and/or 174, it flows through tubes 176, into sample chamber 160, and contacts sensor chip 110.

Figure 3:
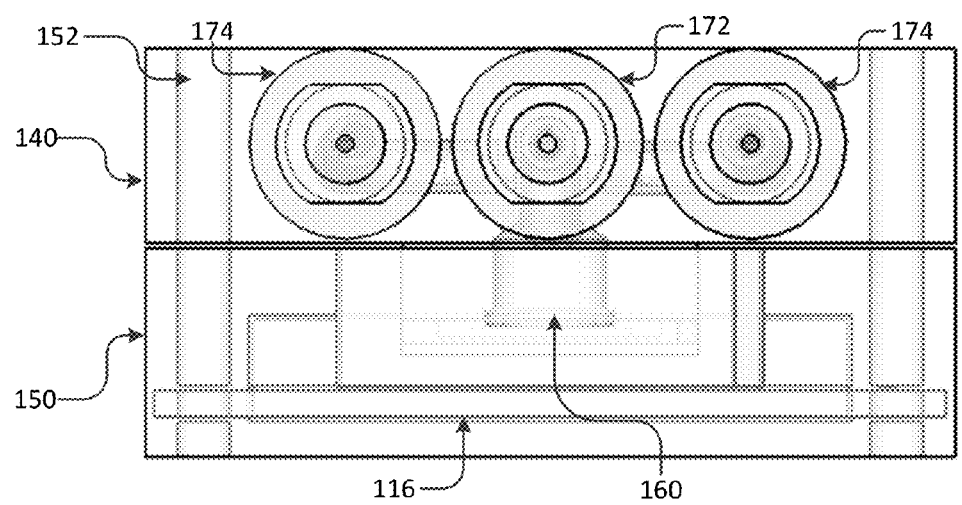
FIG. 3 illustrates a back view of a biological sample analysis device consistent with embodiments disclosed herein.

FIG. 3 illustrates a back view of a biological sample analysis device 100. In the non-limiting example embodiment illustrated by FIG. 3, three sample delivery flanges are located on an external surface of the casing and are configured to hydraulically couple to an external sample deliver system. In some examples, flanges 174 may be input flanges and flange 172 may be an exit flange. For example, one of flanges 174 may be a biological sample input flanges, and one of flanges 174 may be a cleaning solution input flange.

In other examples, only two flanges may be used, while in some examples, more than three flanges may be used. Other mechanisms for delivering a biological sample to the sensor chip may be used. For example, sensor chip 110 may be dipped in a biological sample stored in a test tube, dewar, cup, catheter bag, or other container. Alternatively, sensor chip 110 may be located within a tube designed to carry the biological sample, or may be configured on a test strip or card and passed directly through the biological sample (e.g. similar to a pregnancy test strip).

Figure 4:
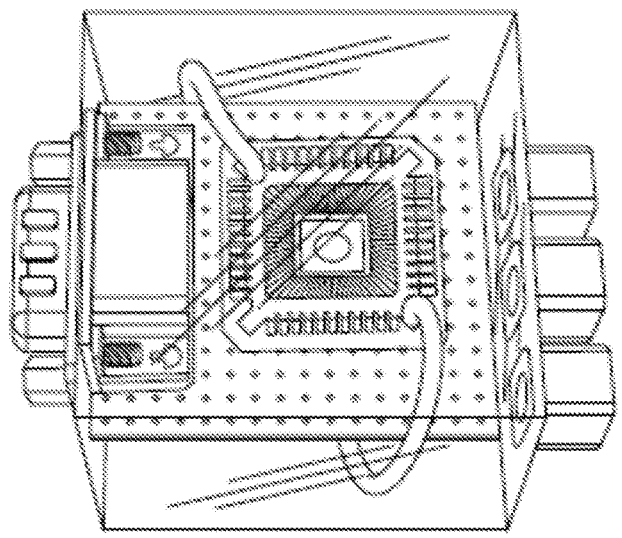
FIG. 4 is a photograph of an example biological sample analysis device consistent with embodiments disclosed herein.

FIG. 4 is a photograph of an example biological sample analysis device. As illustrated by FIG. 4, the casing system may be an acrylic casing or a plastic casing. In other embodiments, the casing system may comprise composite materials, metal, rubber, silicone, glass, resin, or other liquid tight materials as known in the art.

Figure 5:
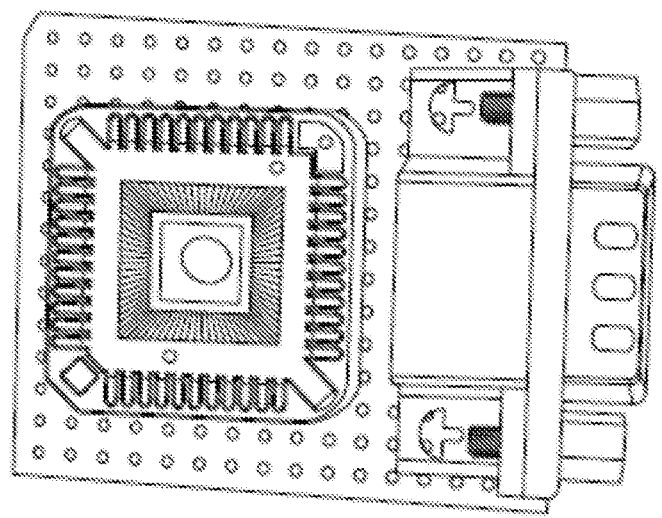
FIG. 5 is a photograph of an electronic biological sample sensor system from an example biological sample analysis device consistent with embodiments disclosed herein.

FIG. 5 is a photograph of an electronic biological sample sensor system from an example biological sample analysis device. As illustrated by FIG. 5, a sensor chip may be wire bonded to a chip carrier, the chip carrier may be coupled to a carrier socket, and the carrier socket may be mounted on a circuit board (e.g. a bread board). The circuit board may then couple to an electronic connector. In some embodiments, the chip carrier is a 44-pin chip carrier. The circuit board may be custom made to electrically couple to the pins from the chip carrier to the connector. In many embodiments, the electronic biological sample sensor system is assembled such that each transistor from the sensor chip completes an electrical circuit through the chip carrier, carrier socket, circuit board, and/or electrical connector. For example, the electrical connector may comprises connector leads for both $V_{DS}$ and $V_{GS}$, to supply drain-source voltage and gate-source bias to each of the transistors on the sensor chip. The electrical connector may further comprise multiple channel leads to monitor and/or measure current flow across each of the transistors independently, such that each channel monitors a different transistor. In some examples, the connector is a sub-D connector.

Figure 6:
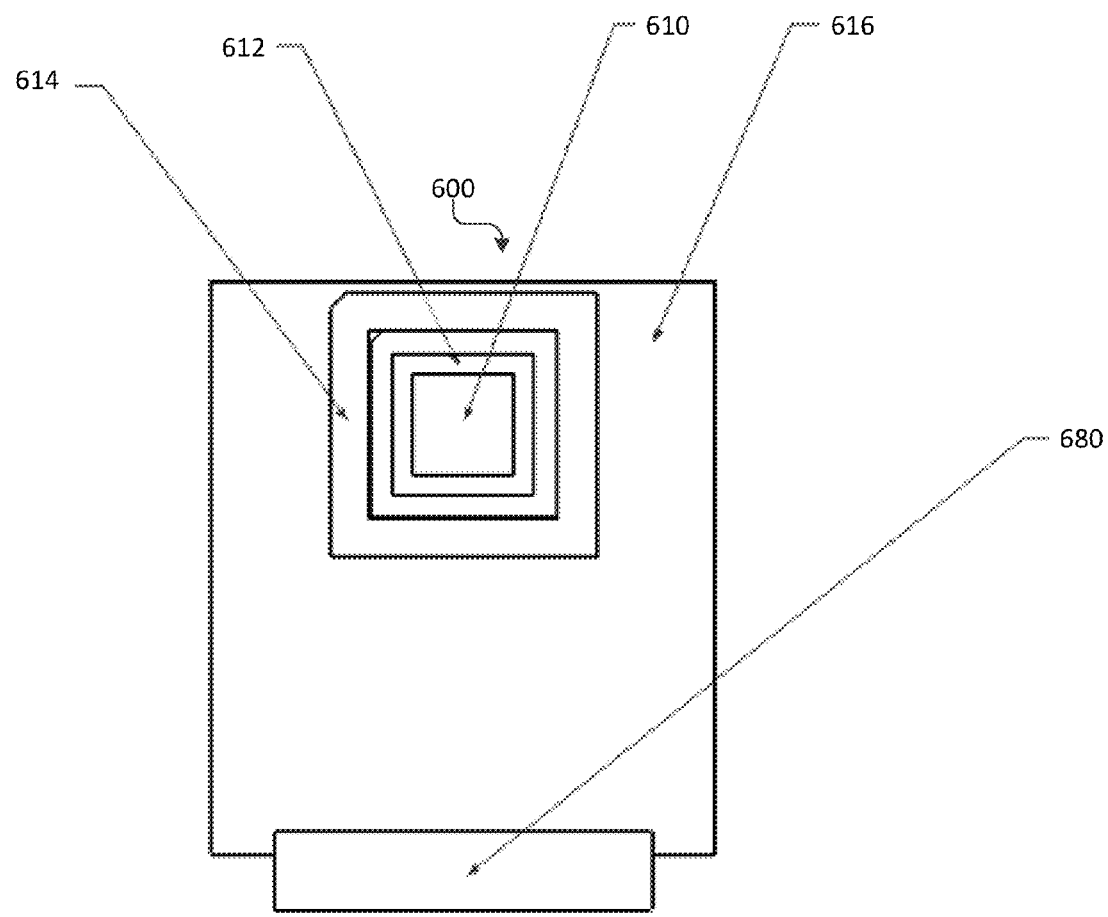
FIG. 6 illustrates a top view of an electronic biological sample sensor system from an example biological sample analysis device consistent with embodiments disclosed herein.

FIG. 6 illustrates a top view of an electronic biological sample sensor system from an example biological sample analysis device. As illustrated, an example electronic biological sample sensor system 600 may comprise sensor chip 610, chip carrier 612, carrier socket 614, circuit board 616, and electrical connector 680. Alternative embodiments may include just sensor chip 610 and electrical connector 680. In some embodiments, an electronic biological sample sensor system is a single integrated circuit comprising one or more Graphene transistors, each transistor being configured to expose the Graphene transistor gates to an external environment (e.g. to a liquid sample resting on a top surface of the Graphene transistor). The electronic biological sample sensor system may further comprise $V_{DS}$ and $V_{GS}$ circuit connections to supply drain-source voltage and gate-source bias to each transistor, as well as at least one electrical channel for monitoring and/or measuring current flow through each transistor.

Figure 7:
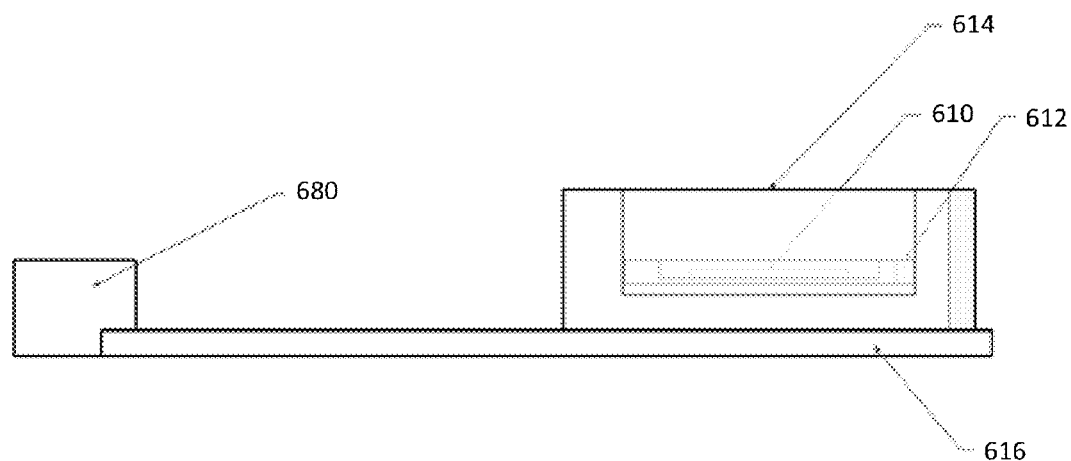
FIG. 7 illustrates a side view of an electronic biological sample sensor system from an example biological sample analysis device consistent with embodiments disclosed herein.

FIG. 7 illustrates a side view of an electronics assembly from an example biological sample analysis device similar to the device illustrated in FIG. 6. Referring to FIG. 7, circuit board 616 may provide electrical connections between electrical connector 680 and sensor chip 610 through chip carrier 612 and carrier socket 614, and may also provide structural support to sensor chip 610, chip carrier 612, and/or carrier socket 614. For example, when sensor chip 610 is bonded to chip carrier 612 and chip carrier 612 is inserted in socket 614, the structural bond between circuit board 616 and carrier socket 612 provides a rigid base for and maintains the structural location of chip carrier 612 and sensor chip 610.

Figure 8:
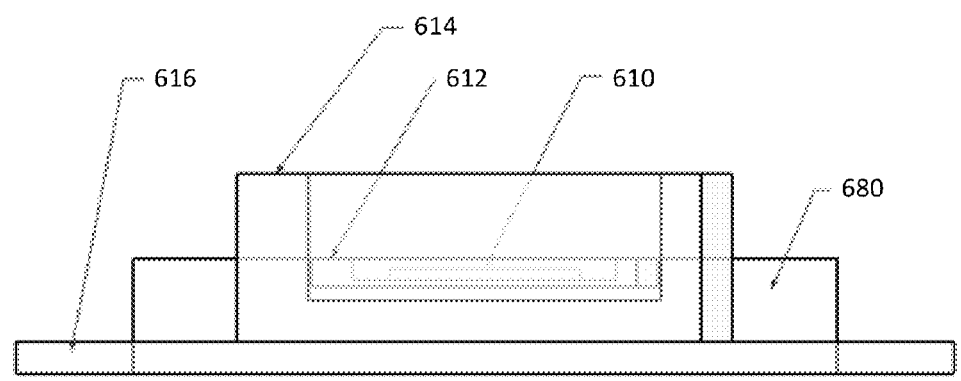
FIG. 8 illustrates a back view of an electronic biological sample sensor system from an example biological sample analysis device consistent with embodiments disclosed herein.

FIG. 8 illustrates a back view of an electronics assembly from an example biological sample analysis device similar to the device illustrated in FIGS. 6 and 7. Referring to FIG. 8, sensor chip 610 may be centrally located with respect to circuit board 616, carrier socket 614, and/or chip carrier 612.

Figure 9:
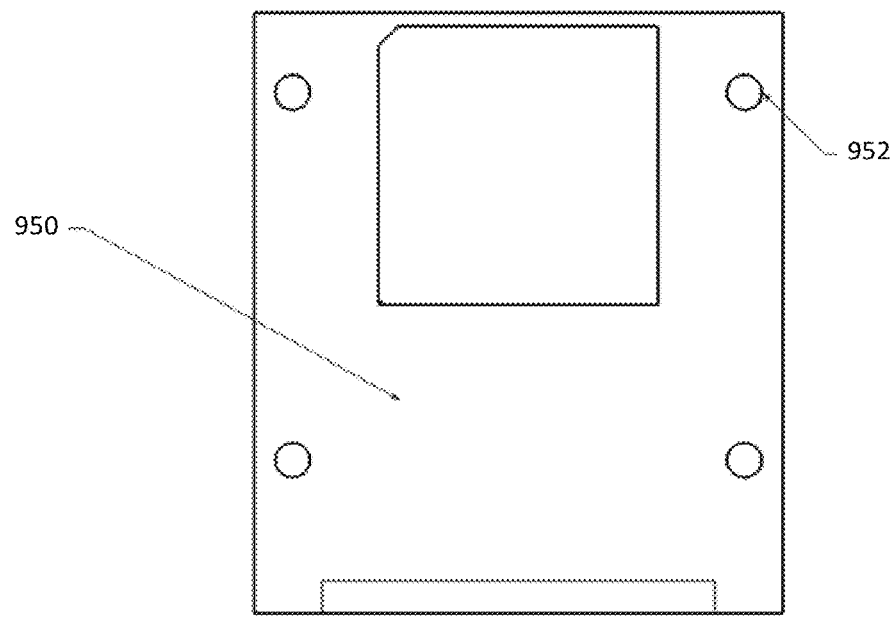
FIG. 9 illustrates a top view of a lower cartridge assembly from an example biological sample analysis device consistent with embodiments disclosed herein.

FIG. 9 illustrates a top view of a lower cartridge assembly from an example biological sample analysis device. Lower cartridge casing 950 may comprise molded or machined plastic, acrylic, glass, ceramic, composite, rubber, metal, or other materials that would be water tight and provide a sterile environment for a biological sample. In some examples, lower cartridge casing 950 comprises thermosetting plastics such as epoxy, polyester or polyurethane or from thermoplastics such as acrylic, polyvinyl chloride or polytetrafluoroethylene (Teflon). Mounting structures 952 may be pins protruding from the casing to mount and align with an upper cartridge assembly, or alternatively, may be holes to accept alignment and/or mounting pins, posts, or screws from the upper cartridge assembly. Other alignment and/or fastening mechanisms may be used to align and secure the upper cartridge assembly with the lower cartridge assembly.

Figure 10:
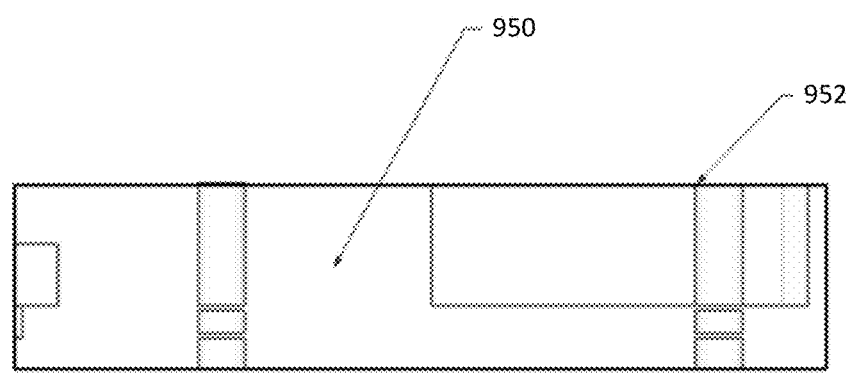
FIG. 10 illustrates a side view of a lower cartridge assembly from an example biological sample analysis device consistent with embodiments disclosed herein.

FIG. 10 illustrates a side view of a lower cartridge assembly from an example biological sample analysis device similar to the device illustrated in FIG. 9. Referring to FIG. 10, example mounting holes 952 may extend vertically through the lower cartridge assembly.

Figure 11:
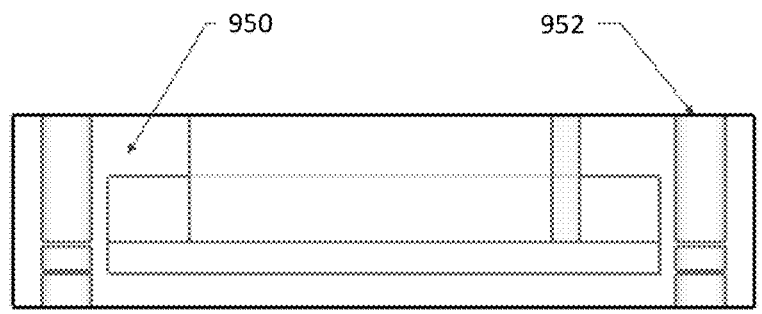
FIG. 11 illustrates a back view of a lower cartridge assembly from an example biological sample analysis device consistent with embodiments disclosed herein.

FIG. 11 illustrates a back view of a lower cartridge assembly from an example biological sample analysis device similar to the device illustrated in FIG. 9. Referring to FIG. 11, openings in casing 950 may be located and configured to accept the electronic biological sample sensor system described in FIGS. 6-8.

Figure 12:
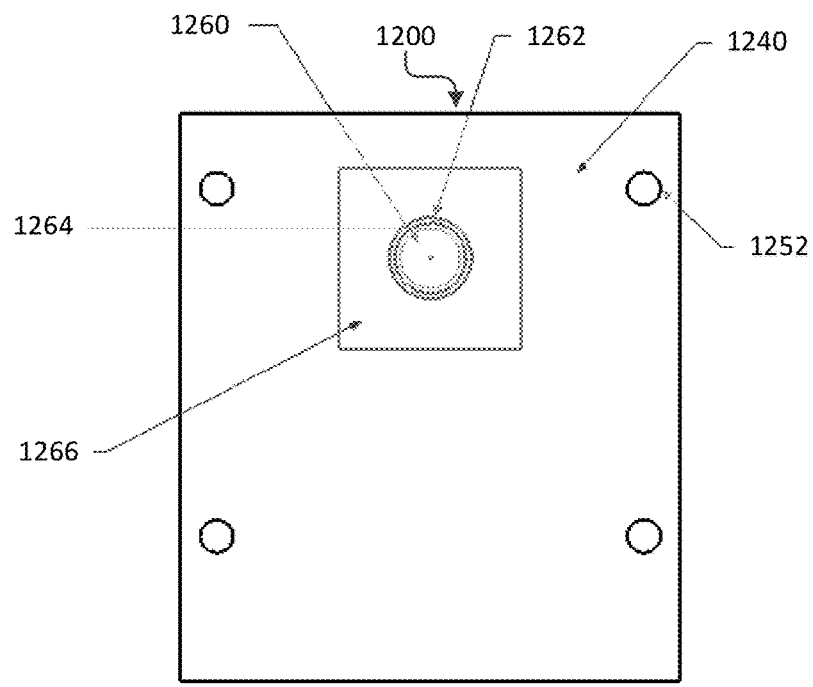
FIG. 12 illustrates a upper view of an upper cartridge assembly from an example biological sample analysis device consistent with embodiments disclosed herein.

FIG. 12 illustrates a top view of a upper cartridge assembly from an example biological sample analysis device. Upper cartridge casing 1240 may comprise molded or machined plastic, acrylic, glass, ceramic, composite, rubber, metal, or other materials that would be water tight and provide a sterile environment for a biological sample. In some examples, upper cartridge casing 950 comprises thermosetting plastics such as epoxy, polyester or polyurethane or from thermoplastics such as acrylic, polyvinyl chloride or polytetrafluoroethylene (Teflon). Mounting structures 1252 may be pins protruding from the casing to mount and align with the lower cartridge assembly, or alternatively, may be holes to accept alignment and/or mounting pins, posts, or screws from the lower cartridge assembly. Other alignment and/or fastening mechanisms may be used to align and secure the upper cartridge assembly with the lower cartridge assembly.

Still referring to FIG. 12, upper cartridge assembly may further comprise biological sample chamber 1260, O-ring groove 1262, O-ring 1264, and/or cartridge body alignment tab 1266. For example, sample chamber 1260 may be configured to hold a liquid biological sample when sealed on a bottom side by the sensor chip from the electronic biological sensor system. O-ring 1264 may be located inside O-ring groove 1262 and configured to form a seal between sample chamber 1260 and the sensor chip when the upper and lower cartridge assemblies are secured together. Cartridge body alignment tab 1266 is shaped to fit inside a similarly shaped socket on the lower cartridge assembly to align the upper and lower cartridge assemblies.

Figure 13A:
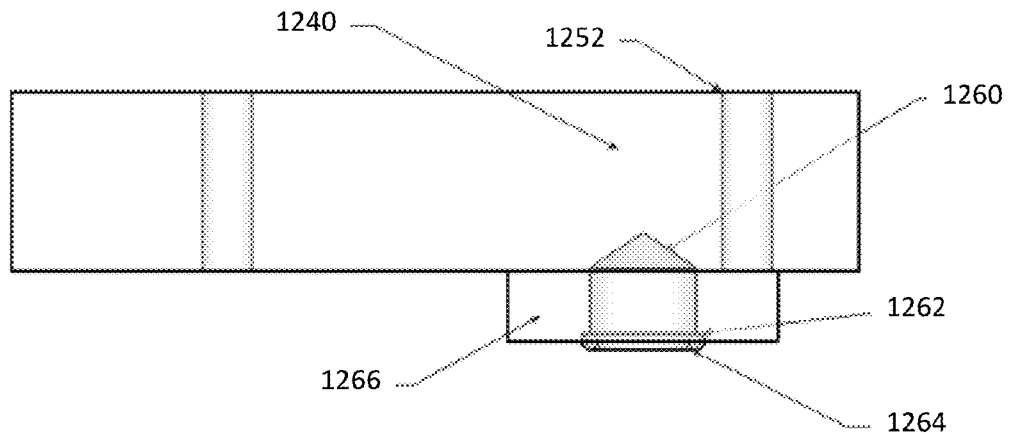
FIG. 13A illustrates a side view of an upper cartridge assembly from an example biological sample analysis device consistent with embodiments disclosed herein.

FIG. 13A illustrates a side view of an upper cartridge assembly from an example biological sample analysis device similar to the device illustrated in FIG. 12. Referring to FIG. 13A, sample chamber 1260 and cartridge body alignment tab 1266 may protrude downward from the upper cartridge assembly.

Figure 13B:
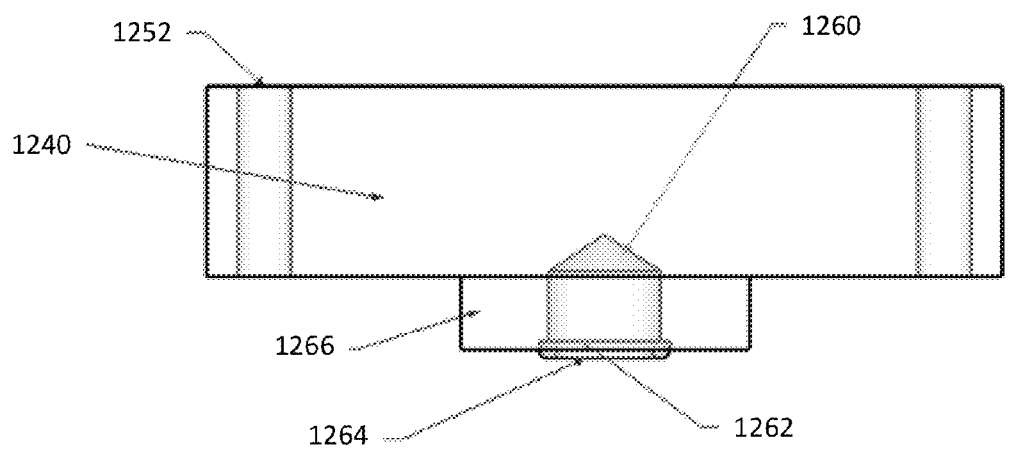
FIG. 13B illustrates a back view of an upper cartridge assembly from an example biological sample analysis device consistent with embodiments disclosed herein.

FIG. 13B illustrates a back view of a top cartridge assembly from an example biological sample analysis device similar to the device illustrated in FIGS. 12 and 13A. Referring to FIG. 13B, sample chamber 1260 and cartridge body alignment tab 1266 may be centrally located within the upper cartridge assembly.

Figure 14:
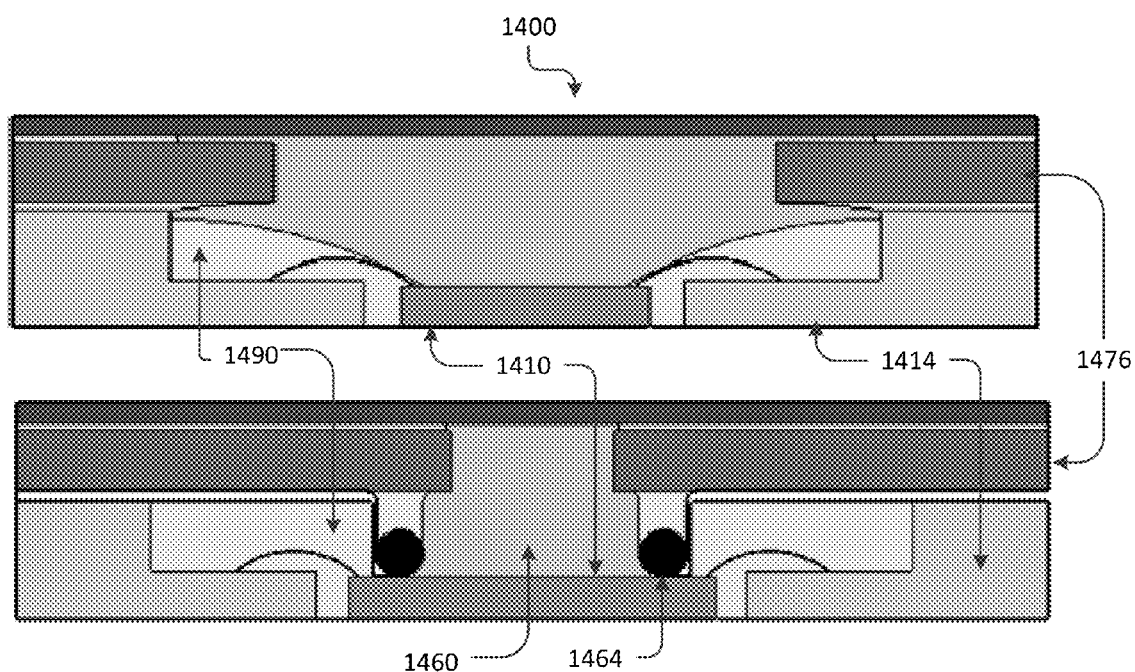
FIG. 14 illustrates a side view of a sample chamber from an example biological sample analysis device consistent with embodiments disclosed herein.

FIG. 14 illustrates a side view of a sample chamber epoxied or molded onto a chip carrier from an example biological sample analysis device clamped to a sensor chip from an example biological sample analysis device. Referring FIG. 14, sample chamber 1400 comprises a molded solid material (e.g. molded plastic) 1490 configured to hold a liquid biological sample. Sensor chip 1410 is located on a lower side of sample chamber 1400 to complete a seal such that, if a liquid biological sample is placed in the sample chamber, gravity will cause the liquid biological sample contact a top surface of sensor chip 1410. Sensor chip 1410 may be secured in sample chamber 1400 using epoxy, molded plastic, or another moldable or formable solid material that may be configured to form a liquid-tight and sterile seal with sensor chip 1410. Sensor chip 1410 may also be forced or clamped against O-ring 1464 to form a liquid-tight and sterile seal. As illustrated by FIG. 14, tubing 1476 may be configured to deliver a liquid biological sample into sample chamber 1400.

Figure 15:
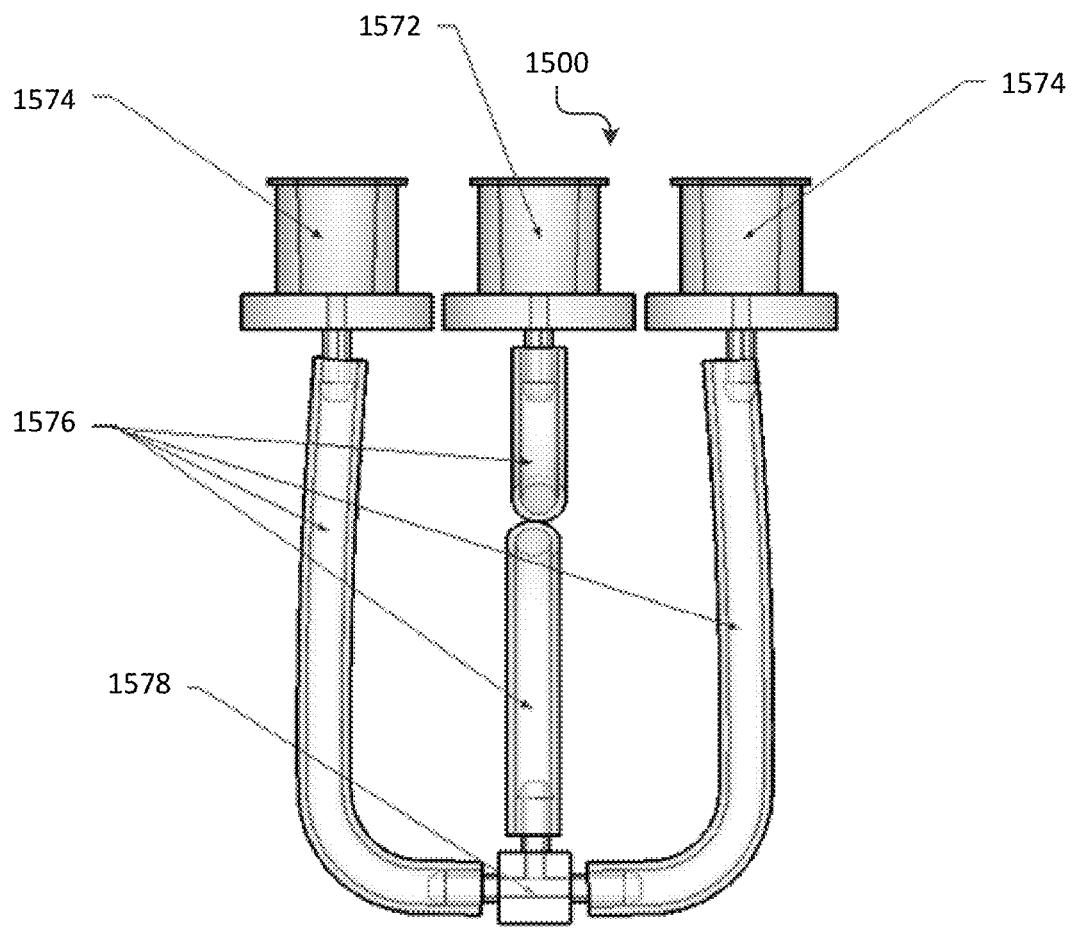
FIG. 15 illustrates a top view of a liquid handling assembly from an example biological sample analysis device consistent with embodiments disclosed herein.

FIG. 15 illustrates a top view of a liquid handling assembly from an example biological sample analysis device. Liquid handling assembly 1500 may comprise one or more tubes 1576 and one or more flanges 1572 and 1574. Flanges 1572 and 1574 are configured to hydraulically connect liquid handling assembly 1500 to an external liquid source. For example, flanges 1574 may accept input from a liquid biological sample source and/or a cleaning source to enable flushing of the liquid handling system with a cleaning solution (e.g. saline). Flange 1572 may be a liquid exhaust flange to enable liquid handling system 1500 to exhaust the biological sample or cleaning solution. Flanges 1572 and 1574 may be Luer fittings, for example. Tubes 1576 may be hydraulically coupled with one or more junction connectors 1578. Liquid handling assembly 1500, and biological sample chamber 1260 illustrated in FIGS. 12-14, may be cleaned with a cleaning solution and/or with steam or chemical sterilization (e.g. bleach, ozone, or hydrogen peroxide).

Figure 16A:
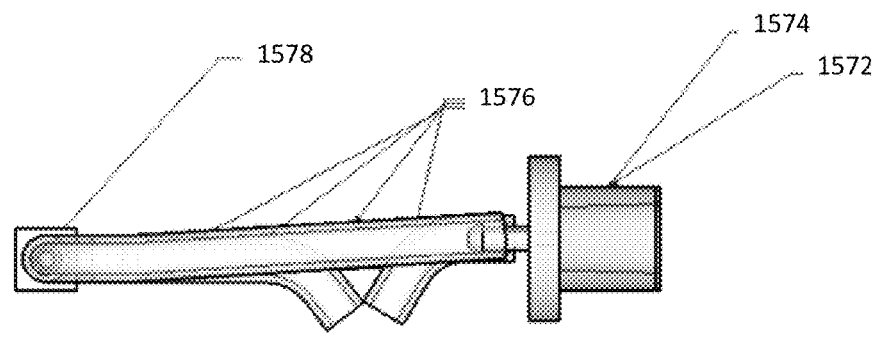
FIG. 16A illustrates a side view of a liquid handling assembly from an example biological sample analysis device consistent with embodiments disclosed herein.
Figure 16B:
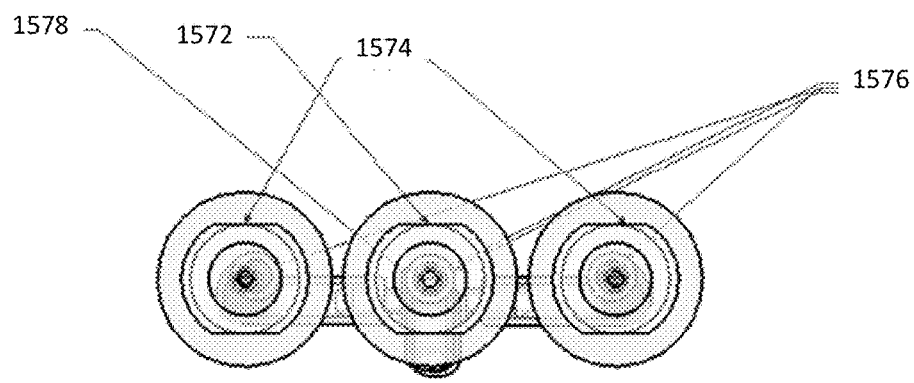
FIG. 16B illustrates a front view of a liquid handling assembly from an example biological sample analysis device consistent with embodiments disclosed herein.

FIG. 16A illustrates a side view and FIG. 16B illustrates a front view of a liquid handling assembly from an example biological sample analysis device from an example biological sample analysis device similar to the liquid handling assembly illustrated in FIG. 15. As illustrated, tube 1576 may couple to flanges 1574 and 1572 with a liquid-tight coupling mechanism such as a burr or form fit coupling. Tubes 1576 also bend downward to deliver a liquid biological sample into the sample chamber.

Figure 17A:
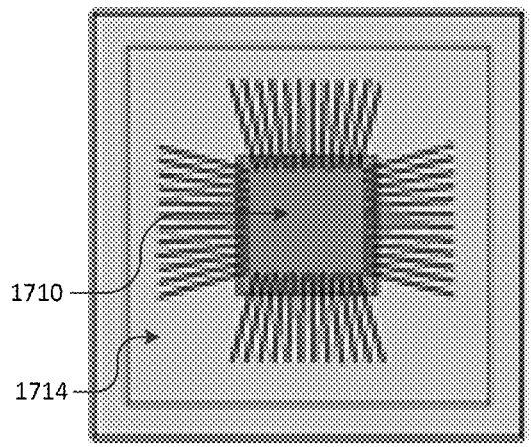
FIG. 17A illustrates a top view of an example biological sample analysis sensor chip wirebonded in a chip carrier consistent with embodiments disclosed herein.
Figure 17B:
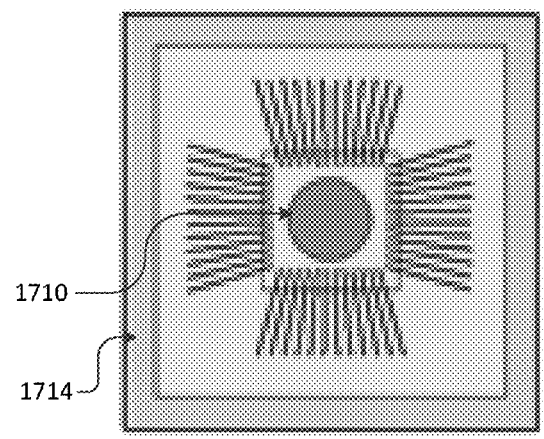
FIG. 17B illustrates a top view of an example biological sample analysis sensor chip covered with a molded plastic cover shaped to form a sample chamber consistent with embodiments disclosed herein.
Figure 17C:
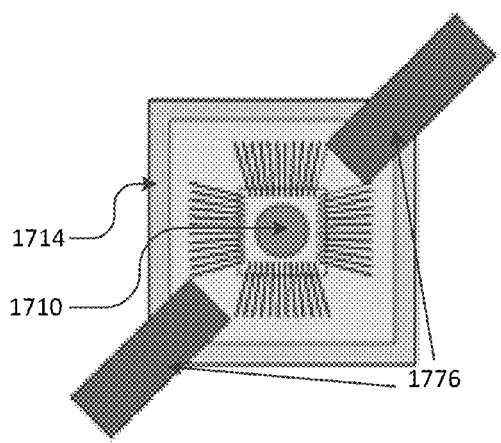
FIG. 17C illustrates a top view of an example biological sample analysis sensor chip covered by a sample chamber that is hydraulically coupled to sample deliver tubing consistent with embodiments disclosed herein.
Figure 17D:
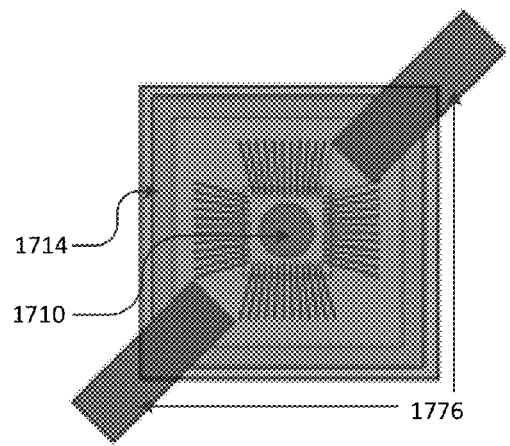
FIG. 17D illustrates a top view of an example biological sample analysis sensor chip covered by a sample chamber and encased in an external casing consistent with embodiments disclosed herein.

FIG. 17A illustrates a top view of an example biological sample analysis sensor chip wirebonded in a chip carrier from an electronic biological sensor system. Sensor chip 1710 may be a Graphene chip with a plurality of Graphene transistors wherein each transistor electrically couples through wire leads to chip carrier 1714. FIG. 17B illustrates a top view of sensor chip 1710 covered with a molded plastic cover shaped to form a sample chamber similar to sample chamber 1400 illustrated in FIG. 14. Accordingly, when a liquid biological sample is introduced into the sample chamber, gravity will cause the biological sample to contact sensor chip 1710. FIG. 17C illustrates a top view of sensor chip 1710, covered with a sample chamber, and hydraulically coupled to tubes 1776 configured to deliver a liquid biological sample into sample chamber 1400. FIG. 17D illustrates a top view sensor chip 1710 covered by a sample chamber and encased in an external casing similar to external casings disclosed in FIGS. 1-4 and 6-14.

Figure 18:
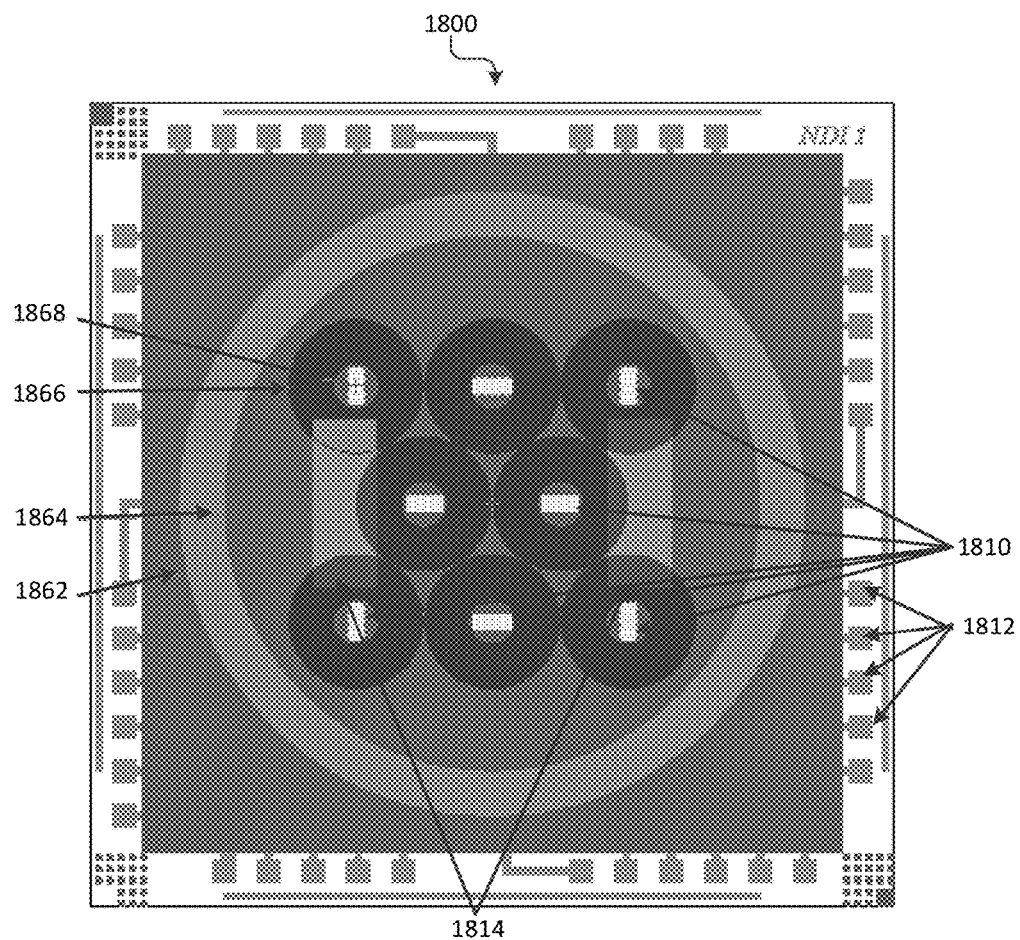
FIG. 18 illustrates a top view of an example biological sample analysis sensor chip consistent with embodiments disclosed herein.

FIG. 18 illustrates a top view of an example biological sample analysis sensor chip as used in an electronic biological sample sensor system. For example, biological sample analysis sensor chip 1800 may comprise one or more transistors 1810. Each transistor 1810 may comprise Graphene. For example, each transistor 1810 may comprise $sp^2$ hybridized Carbon ($Csp^2$) that is a single atomic layer thick, or just a few atomic layers thick. Each Graphene transistor 1810 may further comprise one or more electronic scattering sites, wherein each electronic scattering site comprises Carbon that is $sp^3$ hybridized. $Sp^3$ hybridized Carbon enables covalent bonding with a biomolecule at the $Csp^3$ orbital. The covalently bonded molecules may act as biomarkers wherein predetermined biomarkers will additionally bond to predetermined antibodies generated by a living organism (e.g. a human or a mammal) in response to a particular virus, bacteria, disease, or illness. For example, the Graphene chip may be prepared for chemical functionalization by chemical oxidation with Diazonium salts, Sulfuric Acid, Potassium Permanganate or Hydrogen Peroxide. Antibody attachment may start by linking Carboxylic Acid groups on the Graphene to amine groups on the antibody or linker using 1-Ethyl-3-(3-Dimethylaminopropyl)Carbodiimide (EDC) and N-Hydroxysuccinimide (NHS). A linker molecule may be used when direct attachment to the antibody is not possible. In one example, Streptavidin is used to bind a Biotinylated protein or Nitrotriacetic Acid is used to bind a His-tagged protein. Multiple antibodies can be attached to a single chip by limiting the reaction volume to sufficiently a small drop on top of a group of transistors.

In several embodiments, the Graphene sensor chip may be constructed using a photolithography fabrication process to form Graphene transistors connected to metal contact leads. For example, the Graphene may be a CVD Graphene on a plastic film that is placed on a wafer (e.g. a silicon wafer) and exposed to a solvent (e.g. acetone) to dissolve the plastic and leaving the Graphene on the wafer. The Graphene may then be rinsed (e.g. with isopropyl alcohol, methanol, and/or water) and heated to remove residue. In some examples, the wafer with the Graphene layer is heated for between 30 minutes and four hours. If a shorter time is used, than the wafer with the Graphene layer may be exposed to heat of between 150 degrees C. to 300 degrees C., whereas if a longer heating time is selected, than the wafer with the Graphene layer may be exposed to air at room temperature. Other methods of depositing Graphen on a wafer are possible, including standard material deposition processes as would be known in the art.

One example method for constructing a Graphene sensor chip includes depositing alignment marks and some wiring on a wafer using photolithography, depositing a Graphene layer, then depositing final wiring using photolithography. Another example method for constructing a Graphene sensor chip includes depositing Graphene and depositing all wiring in a single step. The steps described are non-limiting and may be performed in any order. After the deposition of the Graphene and wires, many examples include dicing the wafers into chips, bonding the chips into chip carriers, and loading the chips onto circuit boards. Several examples further include electrically coupling a socket for the chips to an external electrical connector. In some examples, the bonding of the chip to the chip carrier is a wire bonding process. In some examples, the chip carrier is a 44 pin ceramic or plastic chip carrier, but other chip carrier formats are possible as would be known in the art.

In some examples, the circuit boards are configured such that at least two pins are voltage inputs and the remaining pins are measurement channels. For example, one voltage input may be used to set the drain-source bias on the Graphene transistors ($V_{DS}$) and the other voltage input may be used to set the gate-source bias on the Graphene transistors ($V_{GS}$). The $V_{DS}$ lead may electrically couple to the drain electrode on each Graphene resistor, and $V_{GS}$ lead may electrically couple to the gate and/or source electrodes of each Graphene resistor and may be used to set the gate/source bias. Measurement channel leads may then electrically couple to individual Graphene transistors to measure current when the Graphene transistor is exposed to a liquid sample. For example, when biomarkers bonded to the Graphene transistor gate are selected for their bonding properties with specific antibodies. When a specific biomarker bonds with the specific antibody, the conductive properties of the Graphene change, causing that particular transistor to switch on, and allowing current to flow to the transistor's source and respective measurement channel. Graphene transistors on any given sensor chip may be configured with a uniform biomarker designed to bond with a uniform antibody (e.g. an antibody for Lyme disease), or multiple biomarkers may be used for the different Graphene transistors, such that a single sensor chip may detect multiple antibodies present in a single liquid sample.

Any biomarker that is known to bond to a particular antibody may be used in the sensor chip to detect the presence of that antibody. The following non-limiting list includes several example diseases and infections with known antibody-to-biomarker relationships:

Autoimmune Diseases
Hashimoto's thyroiditis
Hyperthyroidism
Multiple sclerosis
Rheumatoid arthritis
Bacterial Infections
*Bacillus anthracis* (anthrax)
*Escherichia coli* (food poisoning)
*Haemophilus influenzae* (bacterial influenza)
*Neisseria gonorrhoeae* (gonorrhea)
*Neisseria meningitides* (meningitis)
*Plasmodium* (malaria)
*Rickettsia prowazekii* (typhus)
*Salmonella enterica* (food poisoning, typhoid)
*Staphylococcus* (food poisoning, staph)
*Streptococcus pneumonia* (pneumonia)
*Treponema pallidum* (syphilis)
Viral Infections
Ebola
Epsein-Bar virus
Hepatitis A, B, C, D, E
Herpes simplex virus (cold sore, herpes)
Herpes zoster (chickenpox, shingles)
HIV
Human coronavirus (common cold)
Influenza (common cold)
Norovirus
Rhinovirus (common cold)
Rotavirus
SARS coronavirus
Variola virus (smallpox)
Cancer Markers
Alpha fetoprotein
beta-2-microglobulin
beta-human chorionic gonadotropin
Calcitonin
Cancer antigen 123
Cancer antigen 125
Cancer antigen 15-3
Cancer antigen 19-9
Cancer antigen 27.29
Carcinoembryonic antigen
Chromogranin A
Cytokeratin
Human chorionic gonadotropin
Osteopontin
Prostate specific antigen Still referring to FIG. 18, transistors 1810 may be organized and/or located within wells 1868 to concentrate a biological sample over the transistors. Wells 1868 may be formed with well structure 1866 that may comprise capillary tubing plastic, rubber, composite, silicon, or other structural materials as known in the art. Each well 1868 may include one or more transistors 1810, and each sensor chip 1800 may include one or more wells 1868, wherein each well may include a homogeneous biomolecule for detection of a particular antibody. In some examples, wells on the same sensor chip may include different biomolecules such that a single sensor chip may be configured to detect a plurality of antibodies. All of the transistors 1810 and wells 1868 make up an antibody detection surface on sensor chip 1800. As illustrated by FIG. 18, the antibody detection surface may be enclosed within O-ring 1864 and configured to be sealed within a sample chamber with a liquid-tight seal. Bond pads, or leads 1812 electrically couple to the transistors, and allow the sensor chip to electrically couple to a chip carrier, carrier socket, circuit board, and/or external electrical connector.

Figure 19:
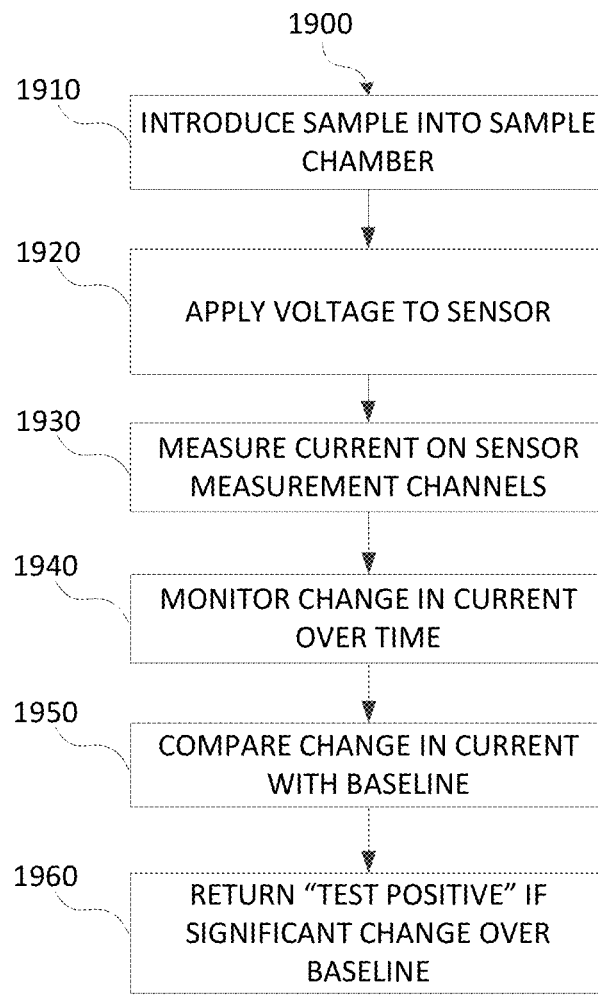
FIG. 19 is a process diagram illustrating a method for electronically testing a biological sample consistent with embodiments disclosed herein.

FIG. 19 is a process diagram illustrating a method for electronically testing a biological sample (e.g. using a biological sample analysis device). A method for electronically testing a biological sample 1900 may include introducing a biological sample into a sample chamber at step 1910. For example, the biological sample may be urine or blood and the sample chamber may be a biological sample chamber and sensor chip similar to embodiments disclosed in FIGS. 1-18. Method 1900 may further include applying a voltage to the sensor chip at step 1920. For example, a voltage may be applied to connector leads electronically coupled to transistors within the sensor chip to supply a drain-source voltage and a gate-source bias. Method 1900 may further include measuring current on sensor measurement channels at step 1930. For example, each sensor measurement channel may be monitored through connector leads electronically coupled to corresponding transistors. Method 1900 may further include monitoring a change in current over time at step 1940, and comparing the change in current with a baseline measurement at step 1950 (e.g. a current measurement taken when the sensor chip was exposed to only saline or another control liquid). Method 1900 may further include returning a "test positive" signal at step 1960 if a threshold change in current over baseline is reached, indicating the presence of an antibody-biomolecule bond at one or more scattering sites as disclosed in FIG. 18.

The steps of measuring current on sensor measurement channels 1930, monitoring changes in current over time 1940, comparing the changes with a baseline measurement 1950, and returning a "test positive" signal may be performed by an electronic biological sample testing module. For example, a biological sample testing module may be a computer module as disclosed in FIG. 21 that includes a processor programmed with one or more computer programs configured to perform the steps disclosed herein. Other steps of method 1900 may be similarly performed by a computer module.

Figure 20:
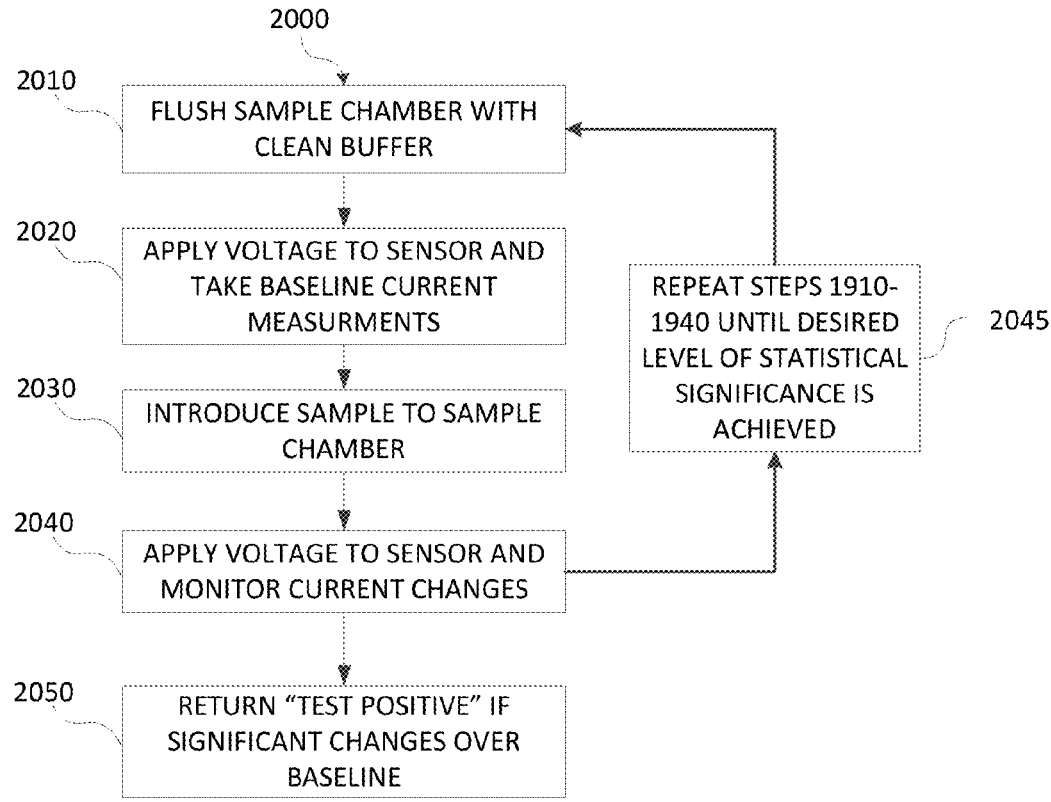
FIG. 20 is a process diagram illustrating a method for electronic biological sample analysis consistent with embodiments disclosed herein.

FIG. 20 is a process diagram illustrating a method for electronic biological sample analysis. A method for electronic biological sample analysis 2000 includes flushing a sample chamber with a clean buffer at step 2010. For example, the sample chamber may be a biological sample chamber similar to embodiments disclosed herein and the clean buffer may be a saline solution or other sterile solution as known in the art. Method 2000 further includes applying voltage to an electronic biological sample sensor system at step 2020. For example, voltage may be applied across the source and drain and source and gate of transistors in a sensor chip. Method 2000 further includes introducing a sample to the sample chamber at step 2030, applying a voltage to the sensor, and monitoring current changes at step 2030. The applied voltage will cause current to vary from a baseline if the biological sample includes antibodies that correspond to biomolecules bonded to scattering sites in the sensor chip transistors. Steps 1910 through 1940 may be repeated multiple times at step 2045 to increase statistical significance of the measurements. Method 2000 may further include returning a "test positive" signal at step 2050 if a the average change in current over baseline exceeds a predetermined threshold level. The steps disclosed in method 2000 may be performed by an electronic biological sample testing module. For example, a biological sample testing module may be a computer module as disclosed in FIG. 21 that includes a processor programmed with one or more computer programs configured to perform the steps disclosed herein.

In some examples, all of the applied and measured voltages are referenced to a common ground. A single device measurement may include applying a voltage (e.g between 0.1V and 1V) to the drain of all of the Graphene transistors ($V_{DS}$) and a voltage (e.g between −1V and 1V) to the liquid in the sensing chamber ($V_{GS}$). The resulting liquid voltage ($V_{REF}$) can be monitored through a reference electrode. The electrical baseline of each of the sensors on the chip can be measured by recording the current on all of the sensor measurement channels when $V_{REF}$ is 0V. $V_{GS}$ can be controlled such that if $V_{REF}$ changes up or down (e.g in a range from −1V to 1V) while holding $V_{DS}$ steady. The current can be measured on all of the sensor measurement channels. For each measurement channel, the resulting data, when considered with a Y-axis of current and an X-axis $V_{REF}$, can be fit with a line. The slope and X-axis intercept of the line can be calculated where the electrical baseline current, slope, and intercept of the fit line form three data points in a measurement vector for each sensor in a device measurement. To increase statistical significance, a device measurement can be repeated multiple times (e.g. 3 to 5 times) to obtain an average value and statistical variance for the measurement vector for each sensor. This process can be automated using a computer module as disclosed herein.

In some examples, a method for electronic biological sample analysis includes connecting a system for electronic biological sample analysis to an electrical system, flushing the system for electronic biological sample analysis with clean serum or buffer, and measuring a baseline device measurement to obtain a baseline set of measurement vectors. The method may further include injecting a biological sample into the system and measuring a device measurement at regular intervals over an incubation period (e.g. every minute for 10, 20, or 30 minutes). The method may further include flushing the system with clean serum or buffer and measuring a device measurement at a regular interval (e.g. every minute for 1, 5, or 10 minutes). The system may then be flushed with clean serum or buffer again and repeating measuring a device measurement at a regular interval. The method may further include comparing the measurement vectors before, during, and after exposing the system to the biological sample and analyzing the date for a significant change in the measurement vector for many similarly functionalized sensors indicating a binding event, which can be reported as a positive identification.

Figure 21:
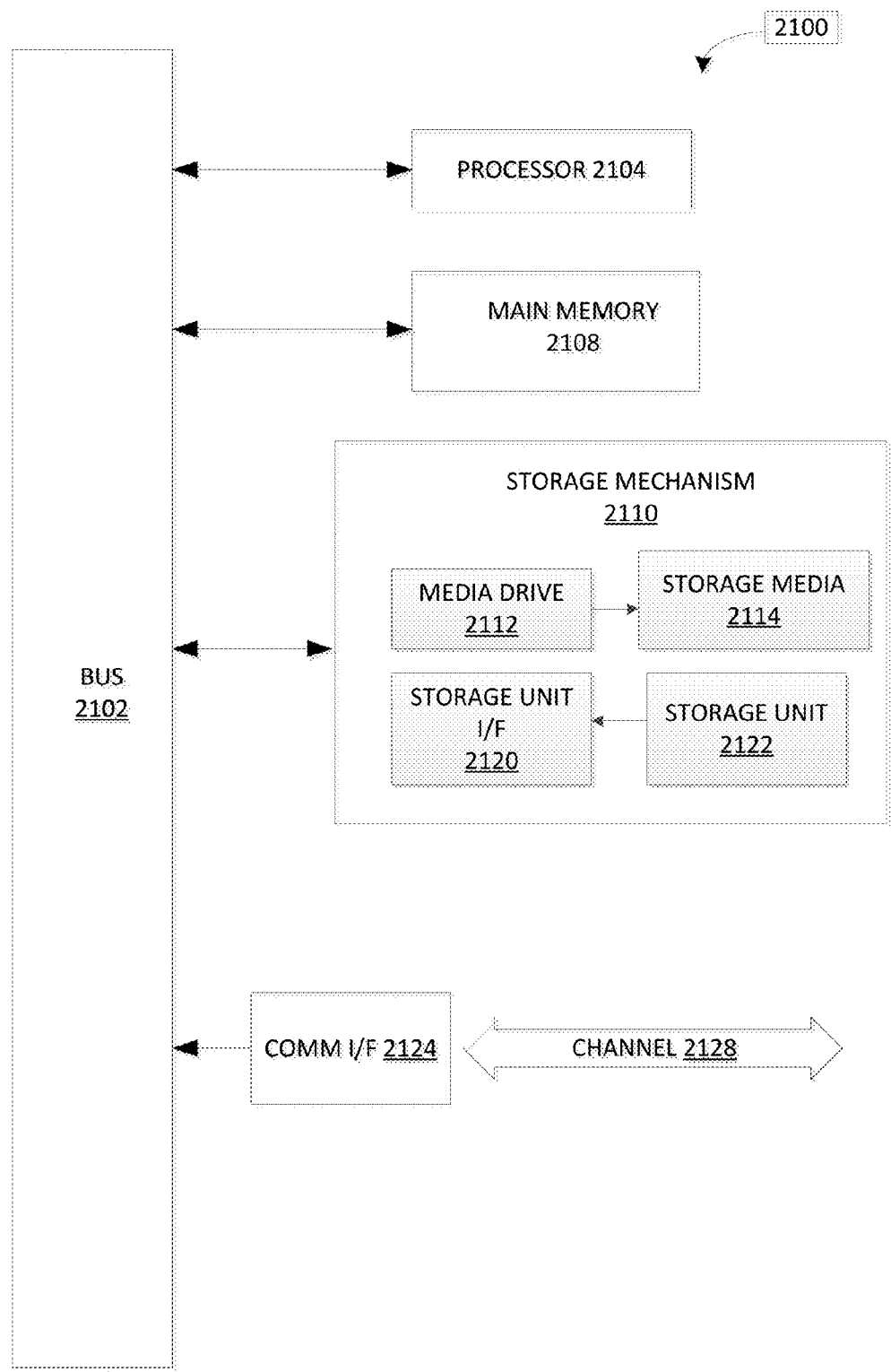
FIG. 21 illustrates an example computing module that may be used to implement various features of the systems and methods disclosed herein.

FIG. 21 illustrates an example computing module that may be used to implement various features of the systems and methods disclosed herein. In one embodiment, the computing module includes a processor and a set of computer programs residing on the processor. The set of computer programs may be stored on a non-transitory computer readable medium having computer executable program code embodied thereon. The computer executable code may be configured to perform one or more steps of the method for electronically testing a biological sample 1900 disclosed in FIG. 19, and/or one or more steps of the method for electronic biological sample analysis 2000 disclosed in FIG. 20.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 21. Various embodiments are described in terms of this example-computing module 2100. After reading this description, it will become apparent to a person skilled in the relevant art how to implement the application using other computing modules or architectures.

Referring now to FIG. 21, computing module 2100 may represent, for example, computing or processing capabilities found within desktop, laptop, notebook, and tablet computers; hand-held computing devices (tablets, PDA's, smart phones, cell phones, palmtops, smart-watches, smart-glasses etc.); mainframes, supercomputers, workstations or servers; or any other type of special-purpose or general-purpose computing devices as may be desirable or appropriate for a given application or environment. Computing module 2100 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 2100 might include, for example, one or more processors, controllers, control modules, or other processing devices, such as a processor 2104. Processor 2104 might be implemented using a general-purpose or special-purpose processing engine such as, for example, a microprocessor, controller, or other control logic. In the illustrated example, processor 2104 is connected to a bus 2102, although any communication medium can be used to facilitate interaction with other components of computing module 2100 or to communicate externally.

Computing module 2100 might also include one or more memory modules, simply referred to herein as main memory 2108. For example, preferably random access memory (RAM) or other dynamic memory, might be used for storing information and instructions to be executed by processor 2104. Main memory 2108 might also be used for storing temporary variables or other intermediate information during execution of instructions to be executed by processor 2104. Computing module 2100 might likewise include a read only memory ("ROM") or other static storage device coupled to bus 2102 for storing static information and instructions for processor 2104.

The computing module 2100 might also include one or more various forms of information storage mechanism 2110, which might include, for example, a media drive 2112 and a storage unit interface 2120. The media drive 2112 might include a drive or other mechanism to support fixed or removable storage media 2114. For example, a hard disk drive, a solid state drive, a magnetic tape drive, an optical disk drive, a CD or DVD drive (R or RW), or other removable or fixed media drive might be provided. Accordingly, storage media 2114 might include, for example, a hard disk, a solid state drive, magnetic tape, cartridge, optical disk, a CD or DVD, or other fixed or removable medium that is read by, written to or accessed by media drive 2112. As these examples illustrate, the storage media 2114 can include a computer usable storage medium having stored therein computer software or data.

In alternative embodiments, information storage mechanism 2110 might include other similar instrumentalities for allowing computer programs or other instructions or data to be loaded into computing module 2100. Such instrumentalities might include, for example, a fixed or removable storage unit 2122 and a storage interface 2120. Examples of such storage units 2122 and storage interfaces 2120 can include a program cartridge and cartridge interface, a removable memory (for example, a flash memory or other removable memory module) and memory slot, a PCMCIA slot and card, and other fixed or removable storage units 2122 and storage interfaces 2120 that allow software and data to be transferred from the storage unit 2122 to computing module 2100.

Computing module 2100 might also include a communications interface 2124. Communications interface 2124 might be used to allow software and data to be transferred between computing module 2100 and external devices. Examples of communications interface 2124 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 2124 might typically be carried on signals, which can be electronic, electromagnetic (which includes optical) or other signals capable of being exchanged by a given communications interface 2124. These signals might be provided to communications interface 2124 via a channel 2128. This channel 2128 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 2108, storage unit 2120, media 2114, and channel 2128. These and other various forms of computer program media or computer usable media may be involved in carrying one or more sequences of one or more instructions to a processing device for execution. Such instructions embodied on the medium are generally referred to as "computer program code" or a "computer program product" (which may be grouped in the form of computer programs or other groupings). When executed, such instructions might enable the computing module 2100 to perform features or functions of the present application as discussed herein.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

What is claimed is:

1. A system for electronic biological sample analysis comprising:
   a biological sample sensor;
   wherein the biological sample sensor comprises a plurality of transistors;
   one or more of the transistors comprises a scattering site; and
   each transistor comprises $sp^2$ hybridized Carbon in the form of Graphene and each scattering site comprises $sp^3$ hybridized Carbon, the $sp^3$ hybridized Carbon being directly covalently bonded to a biomarker, such that if the biomarker is exposed to an infected biological sample while voltage is applied to the transistor, the conductance of the transistor will change.

2. The system of claim 1, wherein the biomarker is an antibody.

3. The system of claim 2, wherein the antibody is a Lyme disease antibody, a cancer antibody, a HIV antibody, a Hepatitis antibody, or a *Bacillus anthracis* antibody.

4. The system of claim 1, wherein each transistor comprises a source lead, a gate lead, and a drain lead, and the source lead, gate lead, and drain lead each electrically couple to an external connector, the external connector configured to supply drain-source voltage, to supply gate-source bias, and to measure source current.

5. The system of claim 1, further comprising a liquid delivery system, the liquid delivery system comprising a sample chamber, wherein a downward facing side of the sample chamber forms an aperture and the aperture contacts and forms a liquid-tight seal with the biological sample sensor, such that when a biological sample is introduced to the sample chamber, the biological sample contacts a top surface of the biological sample sensor.

6. The system of claim 5, further comprising a casing wherein the casing encapsulates the sample chamber and the electronic biological sample sensor, and wherein the casing comprises one or more flanges, each flange hydraulically coupling to the sample chamber.

7. The system of claim 6, wherein the casing comprises plastic.

8. The system of claim 6, wherein the casing comprises a first half and a second half, wherein the sample chamber is located in the first half and the electronic biological sample sensor is located on the second half and wherein the electronic biological sample sensor forms a liquid-tight seal with the sample chamber when the first half is mounted in a closed position on the second half.

* * * * *